United States Patent
Sullivan

(10) Patent No.: US 7,388,213 B2
(45) Date of Patent: Jun. 17, 2008

(54) METHOD OF REGISTERING A BLANK SUBSTRATE TO A PATTERN GENERATING PARTICLE BEAM APPARATUS AND OF CORRECTING ALIGNMENT DURING PATTERN GENERATION

(75) Inventor: Jeffrey S. Sullivan, Castro Valley, CA (US)

(73) Assignee: Applied Materials, Inc., Santa Clara, CA (US)

(*) Notice: Subject to any disclaimer, the term of this patent is extended or adjusted under 35 U.S.C. 154(b) by 249 days.

(21) Appl. No.: 11/233,607

(22) Filed: Sep. 23, 2005

(65) Prior Publication Data

US 2007/0069154 A1  Mar. 29, 2007

(51) Int. Cl.
*G01N 23/00* (2006.01)
(52) U.S. Cl. .............................. 250/492.2; 250/492.1; 250/492.3; 250/491.1; 430/945; 430/942; 430/22
(58) Field of Classification Search ............. 250/491.1, 250/492.1, 492.3, 492.2; 430/945, 942, 22
See application file for complete search history.

(56) References Cited

U.S. PATENT DOCUMENTS

| | | | |
|---|---|---|---|
| 5,798,947 A | 8/1998 | Ye et al. ..................... 361/589 |
| 5,805,866 A * | 9/1998 | Magome et al. ............... 716/19 |
| 6,424,879 B1 | 7/2002 | Chilese et al. ............... 700/121 |
| 6,883,158 B1 * | 4/2005 | Sandstrom et al. ........... 716/19 |
| 7,025,280 B2 * | 4/2006 | Kaushal et al. ............... 236/16 |

FOREIGN PATENT DOCUMENTS

WO    WO 03/010523 A1    2/2001

\* cited by examiner

*Primary Examiner*—Jack I. Berman
*Assistant Examiner*—Michael J Logie
(74) *Attorney, Agent, or Firm*—Shirley L. Church

(57) ABSTRACT

We have developed a method of registration of a particle beam to internal alignment targets present within photoresist areas which are to be imaged. The method does not affect the photoresist, so the quality of pattern produced in the resist after imaging is not affected. The method used for registration of the particle beam to internal alignment targets also can be used to align a pattern in real time, while the pattern is being created, with the internal alignment targets. The real time alignment during creation of a pattern image in the photoresist can be used to correct for drift, or thermal expansion, or gravitational sag, by way of example.

12 Claims, 3 Drawing Sheets

METHOD OF REGISTERING A BLANK SUBSTRATE TO A PATTERN GENERATING PARTICLE BEAM APPARATUS AND OF CORRECTING ALIGNMENT DURING PATTERN GENERATION

FIELD OF THE INVENTION

In general, the present invention relates to a method of registering a blank substrate, including non-exposed photoresist, to a pattern generating particle beam apparatus. The invention also relates to the correction of alignment of a pattern being generated to a planned pattern which is to be generated on the blank substrate. The particle beam may be an electron beam, an ion beam, a proton beam, a neutron beam, an X-ray, or a laser by way of example. It is understood that a laser beam may not be considered to be a particle beam in some applications; however, for purposes of the present application, when a particle beam is referred to, "particle beam" includes lasers. The invention is useful for semiconductor manufacturing in general, and is particularly useful in the production of a lithographic mask (reticle) of the kind used to pattern substrates in the semiconductor industry.

BRIEF DESCRIPTION OF THE BACKGROUND ART

A method which has typically been used to register a particle beam to a photoresist-coated blank substrate or to an existing pattern employs use of the particle beam itself. This approach typically utilizes a back-scatter detector, where particles that experience high-angle scattering events with the target are collected. The particle beam is scanned in a raster pattern over an alignment target, and a back-scatter "image" is generated from the detector signal, where the brightness of each pixel is determined by the number of particles striking the detector in a time period corresponding to that pixel. This self-alignment method is limited by poor contrast with respect to noise. Further, to avoid incidental exposure of a photoresist-coated blank substrate, the alignment targets must be placed outside of the portions of the photoresist which are to be imaged.

When the substrate is a lithographic mask, and the particle beam is comprised of electrons, in a region of a mask covered with chrome, relatively few back-scattered electrons result from the chrome, because the chrome is thin and the scattering cross-section is small, owing to the high electron beam energy. Many more back-scattered electrons result from the underlying silicon dioxide (and other oxides) present in the mask structure, because the silicon dioxide portion of the structure is very thick compared to the chrome layer (about 50,000 times thicker). Consequently, a target area where no chrome is present scatters nearly as many electrons as a region where chrome is present. As a result, use of this technique to determine whether a pattern which is being created is in alignment with alignment targets present inside an area of photomask which is being imaged is difficult, since the back-scatter image of the targets typically provides poor contrast which makes determining of a centroid location of an alignment target difficult. Further, use of an alignment target which is present in an area of photoresist which is being imaged causes exposure of the photoresist, and the pattern which is generated suffers.

When the particle beam used to create the pattern is an electron beam, another problem is the thermal expansion of the substrate during creation of the pattern. This makes it difficult to register an electron beam to write a pattern in a proper relationship to a planned pattern alignment on the substrate, using the electron beam itself as a reference. U.S. Pat. No. 6,424,879 to Chilese et al., issued Jul. 23, 2002, describes an electron beam writing system which includes an electron beam patterning machine operable to emit an electron beam to form a pattern on a substrate. A computer control system, coupled to the electron beam patterning machine, has a plurality of pre-computed distortion maps. Each distortion map describes expected distortions of the substrate caused by exposure of the substrate to the electron beam. The computer control system controls the electron beam patterning machine using the distortion maps in order to adjust for the expected distortions. The invention makes use of one or more pre-computed distortion maps which describe the thermal and/or mechanical responses of a substrate to electron beam patterning. The distortion maps are used, in conjunction with pattern writing data, to determine the distortions expected in a patterning process, so that adjustments can be made. Because the distortion maps are pre-computed, the computational time required to calculate the thermal distortions is significantly reduced.

The concept of correcting for distortions which will occur during writing of an image on a substrate based on data obtained during writing of that same image on an equivalent substrate at an earlier time is also discussed in U.S. Pat. No. 6,883,138 issued to Sandstrom et al. on Apr. 19, 2005. In particular, the invention is said to relate to a method and a system for predicting and correcting geometrical errors in lithography using masks, such as large-area photomasks or reticles, and exposure stations, such as wafer steppers or projection aligners. The method comprises the steps of collecting information about a mask substrate, mask writer, an exposure station, and/or about behavior of a processing step that will occur after the writing of the mask. Further the method comprises predicting, from the combined information, distortions which will occur in the pattern when it is subsequently printed on the workpiece; calculating from the prediction a correction to diminish the predicted distortion, and exposing the pattern onto the mask substrate while applying the correction for the predicted distortions.

Fabrication of a semiconductor device or a photomask/reticle is a complicated process involving a number of interrelated steps which affect the feature placements or the critical dimensions of various patterns produced. Whether the feature placements or the critical dimensions at issue are those of patterns on a semiconductor wafer, or those of patterns on a reticle used to pattern a semiconductor wafer, the semiconductor device may not meet specification if related patterns of materials on multiple layers within the device are not properly aligned. An ability to adjust the alignment of a newly forming pattern relative to alignment targets present inside an area of substrate to be patterned permits compensation for changing process conditions during imaging of the pattern in a photoresist. This makes it possible to correct for drift, thermal expansion, or gravitational sag, for example, during imaging of the photoresist, whether the process is direct semiconductor device manufacturing or reticle (photomask) fabrication. The reproducibility of the manufacturing process itself may be improved, including the process window. Process window refers to the amount process conditions can be varied without having a detrimental outcome on the product produced. The larger the processing window, the greater change permitted in processing conditions without a detrimental affect on the product. Thus, the ability to adjust a pattern alignment to a target present in an area of pattern formation, during that pattern formation is especially valuable in terms of processing window. A broader processing window generally results in a higher yield of in-specification product produced.

It would be highly desirable to be able to use internal pattern alignment targets which are present within areas of a substrate which are to be patterned. It would also be desirable to be able to periodically reassess the relative geometrical locations of a pattern being formed relative to internal alignment targets, so that more precise corrections can be made for drift, thermal expansion, gravitational sag, or other changes which affect the alignment of a forming pattern (an, image in a photoresist, for example) during fabrication.

SUMMARY OF THE INVENTION

We have developed a method of registration of a particle beam to internal alignment targets present within unexposed photoresist areas which are to be imaged. The method does not affect the photoresist, so the quality of pattern produced in the resist after imaging is not affected. The method of registration also makes it possible to align a pattern which is being developed in the photoresist during the creation of the pattern by the particle beam. The method makes use of a position fiducial which can be accurately measured by an optical reader (such as an electron microscope); pattern alignment targets which are present within a photoresist area which is to be pattern imaged; and, a particle beam which can measure the same position fiducial and generate a pattern in the photoresist. The registration of the particle beam to internal alignment targets present within photoresist areas on a blank (non-imaged) substrate is achieved using the position fiducial location in combination with vectors which indicate the location path of the internal alignment targets present within the photoresist areas. Registration of the particle beam with the internal alignment targets periodically, during creation of the particle-beam-generated pattern, continually provides an improvement in the overall alignment of the pattern being created to the with the planned geometrical pattern layout on the substrate. Often the improved alignment is the result of a correction for drift, or thermal expansion, or gravitational sag, or a combination these, which is occurring during creation of the pattern by the particle beam.

To avoid affecting the photoresist by the registration and alignment processes, the position fiducial is scanned/imaged by an optical reader, followed by scanning/imaging of the pattern alignment targets by an optical reader. Locational coordinates for the position fiducial and the pattern alignment targets are calculated, and vectors from the position fiducial to each pattern alignment target are also calculated. Subsequently, the particle beam is used to scan/image the position fiducial. Coordinates are calculated for the particle beam axis. The coordinates for the particle beam axis are used in combination with the locational vectors which were measured by the optical reader with respect to the pattern alignment targets, to register the pattern alignment targets to the particle beam axis. The position fiducial is at a fixed position relative to the substrate and to the pattern alignment targets present on the substrate. The registration of a given planned pattern alignment target to the position fiducial, and the registration of a given point location on a pattern which is being created by the particle beam to the position fiducial may be determined in a matter of seconds. At least 3 pattern alignment target positions must be determined for registration, and additional pattern alignment targets need to be determined to measure distortion. Typically use of at least 8 pattern alignment target positions is recommended for distortion measurement, to assist in alignment of a pattern which is being created by the particle beam. A "real time" assessment of the distortions between the planned pattern and the pattern which is being created can be made in seconds or minutes, where comparisons of more than three optical reader imaging of pattern alignment target locations are made. A real time alignment adjustment of the particle beam being used to create the pattern provides a continual improvement in the overall alignment of the pattern being created to the planned pattern locations on the substrate. An excellent embodiment for use of this technology is in the fabrication of photomask/reticles of the kind used for semiconductor production.

An optical microscope provides higher contrast to noise than the electron beam backscattering method of determining location which was described in the background art. Under the right conditions, greater than 75% of incident light will reflect (and be detected by an optical camera) from a layer of chrome of the kind which is used in the fabrication of reticles, where less than 5% of incident light will be reflected from exposed silicon dioxide regions, for example. In practice, the contrast will depend on the specifics of the substrate and the optics involved, including the illumination. One of skill in the art will be able to envision applications of the method to a variety of substrates, which are considered to be included within the method of the invention. The higher contrast-to noise makes determining the position of the alignment target more accurate.

The use of a position fiducial that can be accurately measured by both an optical microscope and an electron-beam, for example, typically employs a transmission feature fabricated into a semiconductor or metal. This fiducial acts to bridge the independent coordinate systems measured at either the optical microscope or the particle beam. As a consequence, the knowledge of the relative positions of the particle beam column and optical microscope becomes unimportant. The drift between the optical microscope and the particle beam column does not matter because vectors are used as a coordinating system to retain pattern alignments. Further, alignment marks can be placed inside active areas of a photoresist used to fabricate a device or within photoresist active areas during fabrication of a semiconductor device or a reticle/photomask, since appropriate optical illumination will not expose a photoresist which is sensitive to particle beam radiation.

An apparatus which may be used to align a substrate having a non-imaged (blank) photoresist on its surface to a particle beam axis used to generate a pattern image in the photoresist comprises:

a primary beam optical axis in the form of a particle beam axis, which particle beam is used to generate a pattern;

a secondary optical axis in the form of an optical reader such as an optical microscope;

a position fiducial (also referred to as a grid), which is located at a stationary position relative to the substrate; and a controller/computer adapted to control the operation of the particle beam and the optical microscope axis, where the controller/computer is also adapted to calculate at least three vectors from the position fiducial to at least three alignment target locations on a substrate using data input from the secondary optical axis, and wherein the controller coordinates the at least three vectors with a location of the position fiducial measured by the primary optical axis to conform the primary beam optical axis to an alignment with respect to the alignment target locations on the substrate.

The apparatus is useful in registering a blank photoresist-covered substrate with a particle beam, and is useful in aligning a pattern being created by the particle beam with pattern alignment targets present on the substrate during writing of a planned pattern on the substrate using a particle beam.

The use of three alignment target locations permits registration of the primary optical axis relative to the blank photoresist-coated substrate. However, for alignment of the pattern which is being created by the particle beam with alignment target locations on the substrate (where such alignment target locations may be within the area to be patterned), the use of three alignment target locations does not provide any distortion information. Each additional alignment target location determined as a part of the process improves the distortion information available. Typically about 8 to about 16 alignment target locations provides helpful distortion information. Often the fabrication process itself limits the number of alignment target locations which can be measured. In terms of timing for real time alignment and correction of the location of the primary optical axis during pattern writing, the larger the number of measurements which need to be made, the longer the time period required, and this creates a limitation in itself. Typically, the coarse locations of alignment targets with respect to the position fiducial on a substrate are known to better than the field of view of the optical microscope, so that the precise locations of the alignment targets can be determined without first searching for the targets. For purposes of this invention, any method may be used to determine the coarse locations of the alignment targets, for example, precision mechanical alignment of the substrate with respect to the position fiducial, a second optical microscope with a larger field of view (which typically exhibits poorer location accuracy), or tiling several optical microscope images together to create a composite image over a larger extent (area) than a single field of view.

We have developed a method of registering a particle beam axis relative to a blank, unexposed photoresist covered substrate, where at least a portion of the registration targets are present within an area of the blank photoresist which is to be imaged, comprising:

a) providing a primary beam optical axis in the form of a particle beam axis, wherein said particle beam is used to generate a pattern;

b) providing a secondary optical axis in the form of an optical reader axis;

c) providing a position fiducial at a fixed location relative to the substrate (often the position fiducial is located on the substrate stage);

d) providing a controller adapted to control the operation of the particle beam axis and the optical microscope axis, wherein the controller is also adapted to calculate a plurality of vectors from the position fiducial to a plurality of pattern alignment targets present on the substrate;

e) using the secondary optical axis to determine a feature (such as a centroid) location of the position fiducial, and calculating coordinates $x_0$ $y_0$ of the feature location;

f) moving the substrate under the secondary optical axis such that an alignment target is within a field of view of the secondary optical axis, and calculating coordinates $x_1$ $y_1$ of the alignment target location;

g) calculating an alignment vector for the alignment target, which vector is $l_1=(x_1-x_0)x+(y_1-y_0)y$;

h) calculating at least 2 additional alignment vectors for at least 2 additional alignment target locations using steps f) and g);

i) moving the position fiducial under the primary beam optical axis, and scanning a feature (such as a centroid) using the primary beam optical axis in a manner to determine the location of the position fiducial;

j) calculating coordinates $(x'_0, y'_0)$ of the position fiducial for the primary beam optical axis;

k) calculating a location for previously-determined alignment target locations on the substrate with respect to the primary beam optical axis, by applying corresponding location vectors $l_n$, where n is an integer of at least three, to the coordinates $(x'_0, y'_0)$ which represent a starting location of the primary optical axis, whereby the primary optical axis is registered to the pattern alignment targets on the blank photoresist coated substrate.

Typically, when pattern alignment targets ranging from 3 to about 16 in number are used, the time period required for registration ranges from about 10 seconds to about 60 seconds, respectively.

We have also developed a method of aligning a planned particle-beam-generated pattern to pattern alignment targets, wherein at least a portion of the pattern alignment targets are present within an area of the substrate which includes non-exposed photorseist, during writing of the planned pattern by the particle beam. The method comprises:

a) providing a primary beam optical axis in the form of a particle beam axis;

b) providing a secondary optical axis in the form of an optical reader axis;

c) providing a position fiducial at a fixed location relative to the substrate (often the position fiducial is located on the substrate stage);

d) providing a controller adapted to control the operation of the particle beam axis and the optical microscope axis, wherein the controller is also adapted to calculate a plurality of vectors from the position fiducial to a plurality of pattern alignment targets present on the substrate;

e) using the secondary optical axis to determine a feature (such as a centroid) location of the position fiducial, and calculating coordinates $x_0$ $y_0$ of the feature location;

f) moving the substrate under the secondary optical axis such that an alignment target is within a field of view of the secondary optical axis, and calculating coordinates $x_1$ $y_1$ of the alignment target location;

g) calculating an alignment vector for the alignment target, which vector is $l_1=(x_1-x_0)x+(y_1-y_0)y$;

h) calculating at least 2 additional alignment vectors for at least 2 additional alignment target locations using steps f) and g);

i) moving the position fiducial under the primary beam optical axis, and scanning a particle beam from the primary beam optical axis in a manner to determine a feature (such as a centroid) location of the position fiducial;

j) calculating coordinates $(x'_0, y'_0)$ of the position fiducial for the primary beam optical axis;

k) calculating a location for previously-determined alignment target locations on the substrate by applying corresponding location vectors $l_n$, where n is an integer ranging from 3 to about 16, to the coordinates $(x'_0, y'_0)$ which represent a starting location of the primary optical axis; and l) using a plurality of alignment target locations relative to a location of the primary beam optical axis to conform the primary beam optical axis to an alignment with respect to the alignment target locations during writing of a particle-beam-generated pattern on the substrate.

Additional coordinate transforms may be applied to known coordinates (in the primary optical axis coordinate space) with respect to alignment target locations of the pre-existing pattern on the substrate, to correct for scale, orthogonality, or other errors which may become apparent during writing of a new electron-beam-generated pattern on the substrate containing a pre-existing pattern.

DETAILED DESCRIPTION OF THE INVENTION

As a preface to the detailed description, it should be noted that, as used in this specification and the appended claims, the singular forms "a", "an", and "the" include plural referents, unless the context clearly dictates otherwise.

Use of the term "about" herein indicates that the named variable may vary to ±10%.

A substantial improvement has been achieved in registration of a particle beam to a substrate including a blank (non-imaged) photomask, where alignment targets are used as a means of registration. Previously alignment targets were located at the periphery of the substrate so imaging/scanning of the alignment targets would not affect the area of the photoresist to be imaged during patterning of the photoresist. In the present method, the alignment targets used to register the particle beam to the substrate can be located within the areas of the substrate where photoresist to be patterned is present. A position fiducial which can be accurately measured by both an optical microscope and a particle beam axis and at least three alignment targets, at least a portion of which are located within areas of the substrate where photoresist is to be patterned, are used to provide the registration.

In addition, the method which is used to register the alignment targets to the particle beam can also be used to provide a real time alignment of a pattern being created by the particle beam with alignment targets on the substrate.

EXAMPLES

Example One

Figure 1:
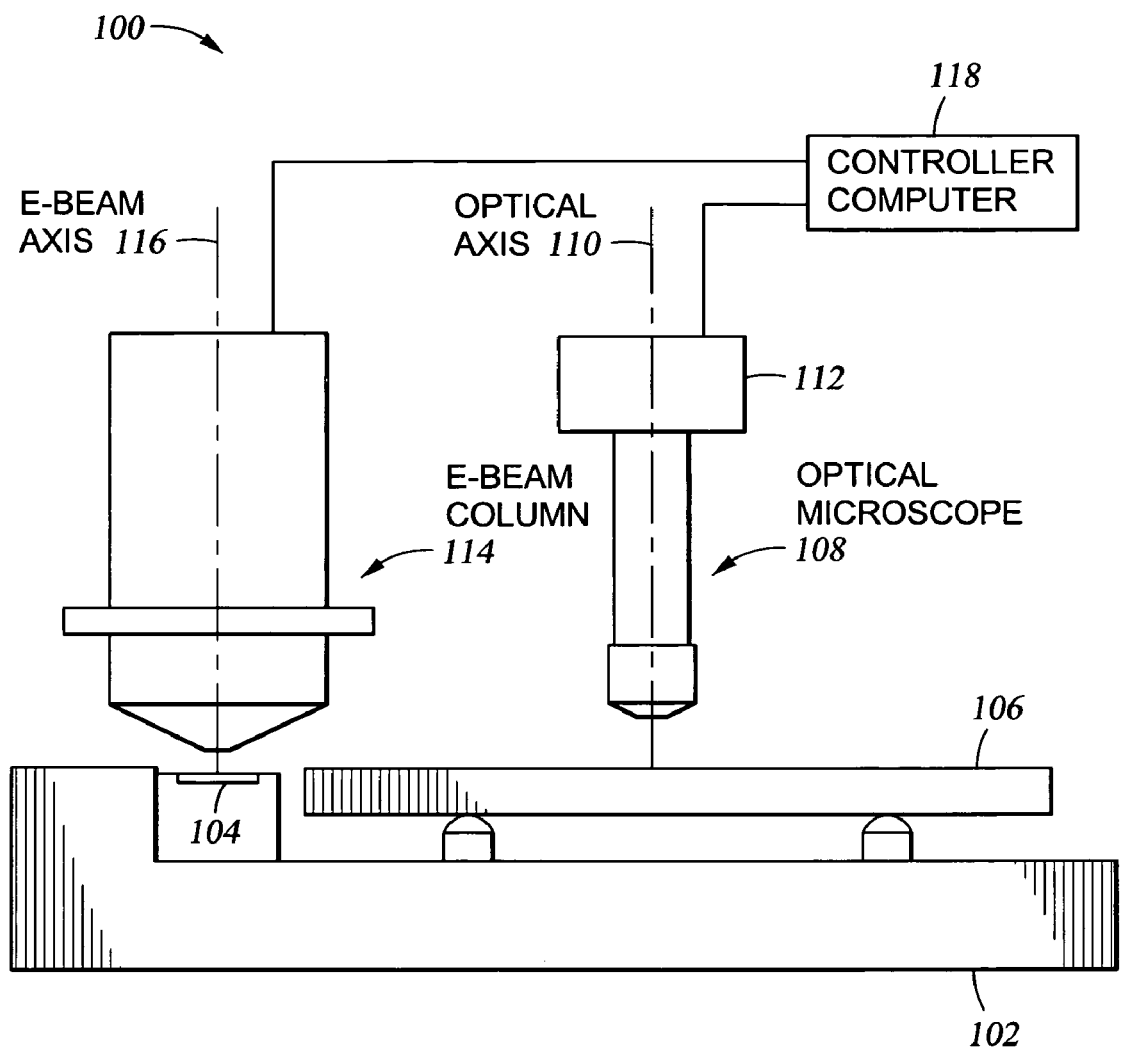
FIG. 1 is an illustration of one embodiment of a lay out of apparatus which can be used to carry out the invention.

FIG. 1 is a schematic drawing which shows an embodiment of the apparatus 100 which may be used to carry out the invention. The substrate 106 on which a pre-existing pattern (not shown) was created is positioned upon a substrate stage 102. The substrate stage also includes a position fiducial 104 which is in a fixed position relative to substrate 106. An optical reader, in the form of an optical microscope 108, including an optical axis 110 is used to scan a position fiducial 104, typically located on substrate stage 102, and alignment targets (not shown) located upon a blank photoresist-coated substrate 106. The scanned data for alignment target locations (not shown) on the blank photoresist-coated substrate 106 are recorded in imager 112 which is a CMOS camera or CCD camera, for example, and (typically digital) data is sent from imager 112 to a controller/computer 118, which calculates coordinates for the alignment target locations and also calculates vectors from the position fiducial 104 to each alignment target location.

With further reference to FIG. 1, the apparatus 100 also includes a particle beam apparatus 114, having an axis 116 which is used to scan the position fiducial 104 initially, and then is used subsequently to create a pattern on the substrate 106. In FIG. 1, the particle beam apparatus 114 is an electron beam. The electron beam collects current that is not blocked by the grid/position fiducial. The electron beam is much smaller than the position fiducial, so most of the time the current is either transmitted or blocked, with edges transmitting fractions. The current transmission data is digitalized and sent to controller/computer 118. The controller/computer 118 uses the particle beam 114 scanned data from position fiducial 104 in combination with the vectors calculated from the optical microscope 108 data to determine the alignment target locations of the pre-existing pattern on the substrate relative to the particle beam 114 axis 116.

Coordinates for the location of alignment target locations (not shown) on substrate 106 relative to the location of the particle beam 114 axis 116 are calculated using the controller/computer 118. The controller/computer 118 is programmed to create a planned pattern which is to be aligned with the alignment targets present on the substrate 106. At the beginning, the creation of a planned pattern is based on the coordinates for the location of the pattern alignment target locations determined by the optical microscope 108 prior to initiation of the planned pattern creation. As pattern creation proceeds on substrate 106, the optical microscope is again scanned over the position fiducial 104 and over the pattern alignment locations, to provide an adjusted location for the pattern alignment target locations relative to position fiducial 104. The electron beam 114 axis 116 is also scanned over position fiducial 104, and new coordinates for the location of pattern feature alignment target locations on the substrate 106 relative to the location of particle beam 114 axis 116 are determined. The controller then calculates any correction to the location at which the new pattern should be created and adjusts the particle beam 114 axis 116 to implement this correction.

The controller/computer 118 referenced above may be any one of a number of controllers of the kind used in the art of registration and alignment in the semiconductor industry.

As previously mentioned, by selecting a photoresist which is not affected by the optical process used to measure the location of the pattern feature alignment targets, it is possible to accumulate registration and alignment information without affecting the creation of the new pattern which is to be aligned with the pre-existing pattern on a substrate.

Example Two

Figure 2:
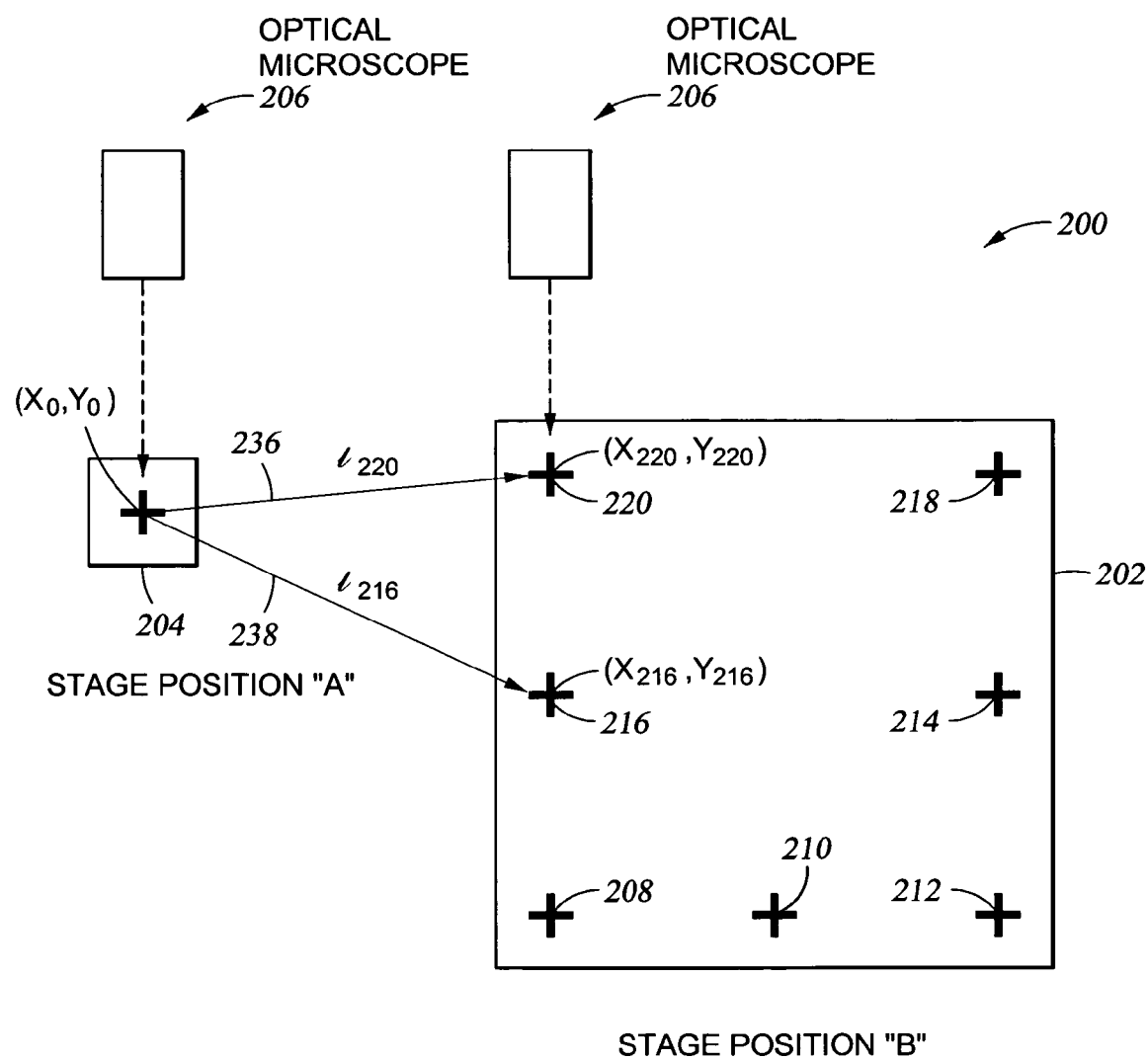
FIG. 2 shows the use of a secondary optical axis 206, such as an optical microscope, to develop a relationship between a position fiducial 204 and the coordinates of alignment target locations, 208-220, for example, of a planned pattern to be written on a substrate, where the relationship includes the determination of vectors, where each vector represents a path between the position fiducial 204 and an alignment target location.

FIG. 2 illustrates the initial registration of pre-existing pattern alignment targets 208, 210, 212, 214, 216, 218, 220 present on a substrate 202, using an optical microscope 206. A position fiducial 204 which is in a fixed position relative to substrate 202 was scanned and imaged by an optical reader, in this case optical microscope 206, while the stage (not shown) was at stage position "A" relative to substrate 202 and position fiducial 204. Coordinates ($x_0$, $y_0$) for a centroid of position fiducial 204 were determined. The stage (not shown) was then mover to position "B" so that optical microscope 206 was at the position shown on FIG. 2 relative to substrate 202 and position fiducial 204. The coordinates ($x_n$, $y_n$) were then determined for a nominal number of pre-existing pattern alignment targets, such as 208, 210, 212, 214, 216, 218, and 220. The minimum number of pattern alignment targets which may be used for registration is three. Typically about 10 pattern alignment targets are used to get a registration of the alignment targets to the optical microscope 206. Additional pattern alignment targets provide additional information, which improves the accuracy of the registration. Further, when the pattern alignment targets are used to align a pattern with a planned pattern geometrical lay out, during creation of the pattern using a particle beam, an increased number of pattern alignment targets provides an improved picture of distortion in the substrate during creation of the pattern. This permits correction of the pattern for such distortions during writing of the pattern. Registration of additional pattern alignment targets require additional time for measurement, and this places limitations on the measurement process. Up to 16 additional pattern alignment targets have been used during photomask/reticle pattern creation, since this is a process which progresses at a speed which permits time for the use of this number of pattern alignment targets. Typically, about 2 seconds are required to register an individual pattern alignment target to the position fiducial.

In FIG. 2, the stage positions "A" and "B" show how the centroid position of the position fiducial 204 was determined using optical microscope 206 at stage position "A", and then the stage was moved to place optical microscope 206 over a pre-existing pattern alignment target 220, which was scanned and imaged by optical microscope 206 and a centroid for the pattern alignment feature target 220 was determined. The imaging of pattern alignment target 220 was done at the first of several stage positions within the general stage position "B". It is not necessary that the precise dimensions of the pattern at location 220 be determined, but only that the centroid of a feature at that location be determined. At this centroid location, coordinates ($x_{220}$, $y_{220}$) were determined. The stage was then moved to place optical microscope 206 over another pattern alignment feature target 216, at a second location within general stage position "B", where the centroid for the pattern alignment feature target 216 was determined. Coordinates ($x_{216}$, $y_{216}$) were calculated. This process was carried out a number of times, to provide coordinates for the centroids of other pre-existing pattern alignment target such as 208, 210, 212, 214, or 218, by way of example. A location vector $l_{220}$, which extends from position fiducial ($x_0$,$y_0$) to pattern alignment feature target 220 was calculated by the computer/controller 118 illustrated with respect to FIG. 1. A location vector $l_{216}$, which extends from position fiducial ($x_0$,$y_0$) to pattern alignment feature target 216 was calculated by the computer/controller 118. The other location vectors were also calculated as well. Once all of the desired location vectors were calculated, the new pattern (not shown) was created to be in alignment with the pre-existing pattern present on substrate 202.

As discussed above, the centroids of the various pre-existing pattern feature alignment targets may be re-measured relative to the position fiducial 204 during the process of writing a pattern. This is necessary if changes in substrate 202 affect the location of the pre-existing pattern feature alignment targets and the location vectors which are used for alignment of the pattern which is being created require correction.

Example Three

Figure 3:
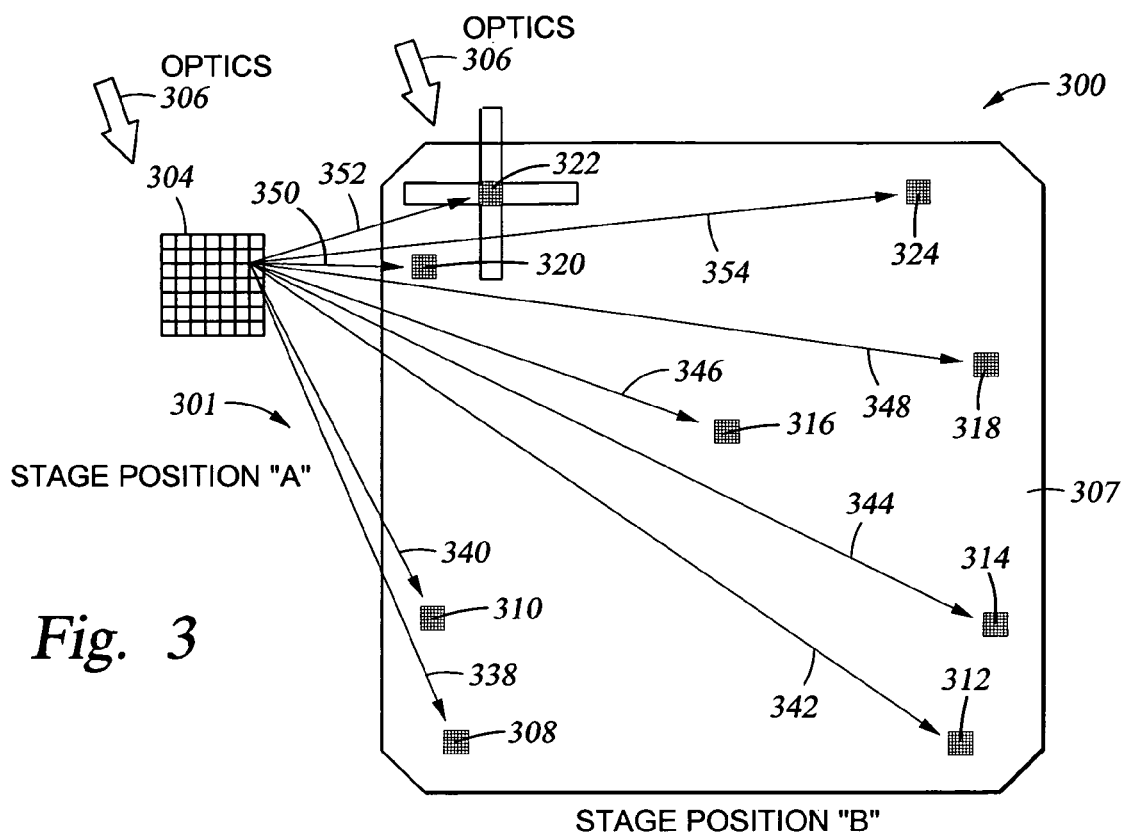
FIG. 3 shows the use of a secondary optical axis 306, as described with respect to optical axis 206 of FIG. 2, to develop a relationship between a position fiducial 304 and alignment target locations, 308-322, for example, of a planned pattern to be written on a substrate. Subsequently, a primary optical axis 366, such as a particle beam axis, is used in combination with the position fiducial 304 and vectors previously determined for the alignment target locations using the secondary optical axis, first to register the particle beam to the target locations 368-382, and subsequently to align a pattern as it is being created by the particle beam with changed target locations (not shown) if there is a change in target locations due to drift, or substrate expansion, or substrate sag, for example, during writing of the planned pattern.
Figure 3:
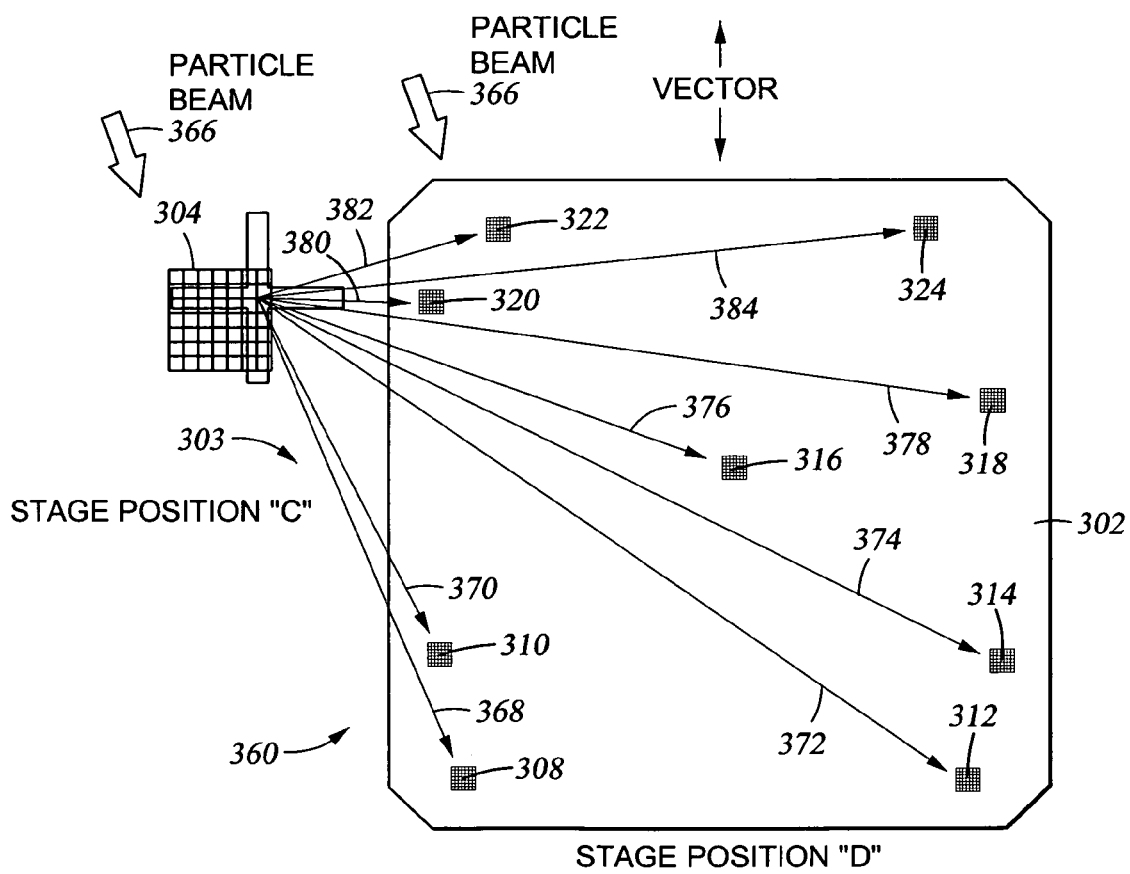

FIG. 3 illustrates the manner in which a relationship between the particle beam axis and the pre-existing pattern feature alignment targets is developed. Periodic reassessment of this relationship during writing of a pattern with the particle beam enables continual alignment of the pattern which is being created with the planned pattern geometrical lay out on the substrate. Schematic 300 of the method elements and system includes an optical section 301 and a particle beam section 303. The optical section 301 mirrors the illustration in FIG. 2. Initial registration of pre-existing pattern alignment targets 308, 310, 312, 314, 316, 318, 320, 322, and 324 present on a substrate 302, the optics image of the pre-existing pattern, is accomplished using an optical reader 306 such as an optical microscope. The imaging of position fiducial 304, which is in a stationary relationship with respect to substrate 302, was carried out when the substrate stage was at position "A" relative to optical reader 306. The optical reader 306, with the substrate stage at position "A" scans the position fiducial 304 and determines a location for a particular feature location for the position fiducial, and the scanned data is used to calculate position fiducial 304 feature coordinates, typically a centroid coordinate ($x_0$, $y_0$). The substrate stage (not shown) is then moved to one of a number of positions within general stage position "B". The optical reader 306 at a first location within general stage position "B" over the substrate 302 may determine feature coordinates for a first pre-existing pattern alignment target such as 322, for example. The substrate stage is then moved to a second location within general stage position "B" to determine feature coordinates for a second pre-existing pattern alignment target such as 320, for example. The optical reader 306 is used to image a number of pre-existing pattern alignment targets, and the data is sent to a controller/computer such as 118 shown in FIG. 1, for calculation of coordinates. The pattern alignment targets are selected to be at locations on the pre-existing pattern which are considered to be the most useful in determining whether pattern distortion of the pre-existing pattern is occurring during formation of a pattern on the blank photoresist-coated substrate. In schematic 300, optical section 301, the coordinates ($x_n$, $y_n$) are determined for a nominal number of pattern alignment target features, such as 308, 310, 312, 314, 316, 318, 320, 322, and 324, for example and not by way of limitation. As previously mentioned, typically about 10 pattern alignment targets are used, so that there is a good indication of distortion which is taking place during writing of a pattern. Up to 16 additional pattern alignment targets have been used during photomask/reticle pattern creation, since this is a process which progresses at a speed which permits time for the use of this number of pattern alignment targets.

The movement from position fiducial 304 to a pattern alignment target feature follows a vector $l_n$. A location vector is calculated for each pattern alignment target feature, for example, location vector $l_{308}$ extends from position fiducial coordinates $(x_0,y_0)$ to pattern alignment feature target 308 coordinates $(x_{308},y_{308})$; location vector $l_{310}$ extends from position fiducial coordinates $(x_0,y_0)$ to pattern alignment feature target 310 coordinates $(x_{310},y_{310})$; and so on. This initial set of position alignment vectors is used in combination with the position fiducial coordinates to provide an initial registration of planned pattern locations on the substrate.

The obtaining of an initial registration of the pre-existing pattern with respect to the particle beam 366 is shown in schematic 300 particle beam section 303. With the substrate stage at position "C", the particle beam 366 was used to scan and image position fiducial 304, inputting data into the controller/computer 118 for calculation of the position fiducial coordinates $(x'_0,y'_0)$. The location vectors $l_{338}, l_{340}, l_{342}, l_{344}, l_{346}, l_{348}, l_{350}, l_{352}$, and $l_{354}$, for example, for the pattern alignment features determined using the optical reader, were then used in combination with the particle beam 366 data for the position fiducial 304, to provide particle beam location vectors $l_{368}, l_{370}, l_{372}, l_{374}, l_{376}, l_{378}, l_{380}, l_{382}$, and $l_{384}$ for the location of pattern alignment features 308, 310, 312, 314, 316, 318, 320, 322, and 324, with respect to the axis of particle beam 366, for example. A combination of the particle beam 366 position fiducial 304 coordinates $(x'_0,y'_0)$ with the particle beam location vectors $l_{368}, l_{370}, l_{372}, l_{374}, l_{376}, l_{378}, l_{380}, l_{382}$, and $l_{384}$ registers the substrate and planned pattern to be written within the particle beam coordinates system. The pattern which is being created while the substrate stage is moved within general stage position "D" can then be aligned with the pattern alignment targets, illustrated as features 308, 310, 312, 314, 316, 318, 320, 322, and 324, for example, on the substrate 302. Since it takes only seconds to scan the position fiducial and an individual pattern alignment target feature using the optical reader 306, to scan the position fiducial with the particle beam, and to convert the vectors from optical reader coordinates to particle beam coordinates, a continual updating of the location of pattern alignment features on the substrate with the location of the axis of the particle beam may be carried out. This continual updating of the alignment between the pre-existing pattern and the particle beam writing the pattern permits a more accurate alignment of the pattern as it is created. Errors in alignment which would have been present due to factors such as drift, or thermal expansion, or gravitational sag, or a combination thereof, can be substantially reduced if not eliminated altogether.

While the invention has been described in detail above with reference to particular schematics and drawings, various modifications within the scope and spirit of the invention will be apparent to those of working skill in this technological field. One skilled in the art, upon reading applicants' disclosure, can make use of various particle beams and registration and alignment hardware and software known in the art to take advantage of the invention disclosed. Accordingly, the scope of the invention should be measured by the appended claims.

We claim:

1. A method of improving registration of a particle-beam relative to a non-exposed, photoresist-coated substrate, wherein at least a portion of the registration targets are present within an area of the non-exposed photoresist which is to be imaged during patterning, said method comprising:
   a) providing a primary beam optical axis in the form of a particle beam axis, wherein said particle beam is used to generate a pattern;
   b) providing a secondary optical axis in the form of an optical reader axis;
   c) providing a position fiducial at a fixed location relative to the substrate;
   d) providing a controller adapted to control the operation of the particle beam axis and the optical microscope axis, wherein the controller is also adapted to calculate a plurality of vectors from the position fiducial to a plurality of pattern alignment targets present on the substrate;
   e) using the secondary optical axis to determine a feature location of the position fiducial, and calculating coordinates $x_0$ $y_0$ of the feature location;
   f) moving the substrate under the secondary optical axis such that an alignment target is within a field of view of the secondary optical axis, and calculating coordinates $x_1$ $y_1$ of the alignment target location;
   g) calculating an alignment vector for the alignment target, which vector is $l_1=(x_1-x_0)x+(y_1-y_0)y$;
   h) calculating at least 2 additional alignment vectors for at least 2 additional alignment target locations using steps f) and g);
   i) moving the position fiducial under the primary beam optical axis, and scanning a feature of said position fiducial using the primary beam optical axis in a manner to determine the location of the position fiducial;
   j) calculating coordinates $(x'_0, y'_0)$ of the position fiducial for the primary beam optical axis; and
   k) calculating a location for previously-determined alignment target locations on the substrate with respect to the primary beam optical axis, by applying corresponding location vectors $l_n$, where n is an integer of at least three, to the coordinates $(x'_0, y'_0)$ which represent a starting location of the primary optical axis, whereby the primary optical axis is registered to the pattern alignment targets on the non-imaged photoresist coated substrate.

2. A method in accordance with claim 1, wherein said particle beam is selected from the group consisting of an electron beam, an ion beam, a laser beam, a proton beam, a neutron beam, or an X-ray.

3. A method in accordance with claim 1 or claim 2, wherein said registration of said particle beam relative to a non-imaged, photoresist-coated substrate is carried out using a number of pattern alignment targets ranging from about 3 targets to about 16 targets.

4. A method in accordance with claim 3, wherein said registration of said particle beam is carried out over a time period ranging between about 10 seconds and about 60 seconds.

5. A method in accordance with claim 1, wherein a controller/computer is used to calculate at least three alignment vectors corresponding to the relationship between the position fiducial coordinates and pattern alignment targets measured using the secondary optical axis, and to relate the particle beam to the pattern alignment targets using a combination of the data related to said coordinates of the position fiduciary for said primary beam optical axis in combination with the at least three alignment vectors.

6. A method of aligning a planned particle-beam-generated pattern to pattern alignment targets, wherein at least a portion of said alignment targets are present within an area of said substrate which includes non-exposed photoresist, during writing of said planned pattern by said particle beam, comprising:
   a) providing a primary beam optical axis in the form of a particle beam axis;
   b) providing a secondary optical axis in the form of an optical reader axis;
   c) providing a position fiducial at a fixed location relative to said substrate;
   d) providing a controller adapted to control the operation of said particle beam axis and said optical microscope axis, wherein the controller is also adapted to calculate a plurality of vectors from said position fiducial to at least three pattern alignment targets present on said substrate;
   e) using said secondary optical axis to determine a feature location of said position fiducial, and calculating coordinates $x_0$ $y_0$ of said feature location;
   f) moving the substrate under the secondary optical axis such that an alignment target is within a field of view of said secondary optical axis, and calculating coordinates $x_1$ $y_1$ of said alignment target location;
   g) calculating an alignment vector for said alignment target, which vector is $l_1=(x_1-x_0)x+(y_1-y_0)y$;
   h) calculating at least 2 additional alignment vectors for at least 2 additional alignment target locations using steps f) and g);
   i) moving said position fiducial under the primary beam optical axis, and scanning a particle beam from said primary beam optical axis in a manner to determine a feature location of said position fiducial;
   j) calculating coordinates $(x'_0, y'_0)$ of said position fiducial for said primary beam optical axis;
   k) calculating a location for alignment target locations on said substrate which locations were previously determined using said secondary optical axis by applying corresponding location vectors $l_n$, where n is an integer ranging from 3 to about 16, to the coordinates $(x'_0, y'_0)$ which represent a starting location of said primary optical axis; and
   l) using a plurality of alignment target locations relative to a location of said primary beam optical axis to conform said primary beam optical axis to an alignment with respect to said alignment target locations during writing of a particle-beam-generated pattern on said substrate.

7. A method in accordance with claim 6, wherein said particle beam is selected from the group consisting of an electron beam, an ion beam, a laser beam, a proton beam, a neutron beam, or an X-ray.

8. A method in accordance with claim 7, wherein said particle beam is an electron beam, and wherein a coordinate transform is applied to known coordinates in a coordinate space of said primary beam optical axis, with respect to alignment target locations on said substrate, to correct for scale, orthogonality, or other errors which become apparent during writing of an electron-beam-generated pattern on said substrate.

9. An apparatus which used to align a substrate having a non-imaged photoresist on its surface to a particle beam axis used to generate a pattern image in the photoresist comprising:
   a primary beam optical axis in the form of a particle beam axis, which particle beam is used to generate a pattern;
   a secondary optical axis in the form of an optical reader such as an optical microscope;
   a position fiducial, which is located at a stationary position relative to said substrate; and
   a controller/computer adapted to control the operation of said particle beam and said optical microscope axis, where said controller/computer is also adapted to calculate at least three vectors from said position fiducial to at least three alignment target locations on a substrate using data input from said secondary optical axis, and wherein the controller coordinates the at least three vectors with a location of said position fiducial measured by the primary optical axis to conform said primary beam optical axis to an alignment with respect to said alignment target locations on said substrate.

10. An apparatus in accordance with claim 9, wherein said particle beam is selected from the group consisting of an electron beam, an ion beam, a laser beam, a proton beam, a neutron beam, or an X-ray.

11. An apparatus in accordance with claim 9, wherein said position fiducial is present on a stage on which said substrate is mounted.

12. An apparatus in accordance with claim 9, wherein said position fiducial is present in a form of a grid.

* * * * *